(12) United States Patent
Link et al.

(10) Patent No.: US 9,944,977 B2
(45) Date of Patent: Apr. 17, 2018

(54) DISTINGUISHING RARE VARIATIONS IN A NUCLEIC ACID SEQUENCE FROM A SAMPLE

(71) Applicant: Raindance Technologies, Inc., Billerica, MA (US)

(72) Inventors: Darren R. Link, Lexington, MA (US); Michael Samuels, Windham, NH (US)

(73) Assignee: Raindance Technologies, Inc., Billerica, MA (US)

( * ) Notice: Subject to any disclaimer, the term of this patent is extended or adjusted under 35 U.S.C. 154(b) by 552 days.

(21) Appl. No.: 14/568,923

(22) Filed: Dec. 12, 2014

(65) Prior Publication Data

US 2015/0167066 A1 Jun. 18, 2015

Related U.S. Application Data

(60) Provisional application No. 61/915,435, filed on Dec. 12, 2013.

(51) Int. Cl.
*C12Q 1/68* (2006.01)
*C07H 21/02* (2006.01)

(52) U.S. Cl.
CPC ......... *C12Q 1/6844* (2013.01); *C12Q 1/6858* (2013.01)

(58) Field of Classification Search
CPC ............ C12Q 1/6858; C12Q 2535/122; C12Q 2563/159; C12Q 2563/179; C12Q 2565/629; C12Q 1/6844
See application file for complete search history.

(56) References Cited

U.S. PATENT DOCUMENTS

2015/0247191 A1* 9/2015 Zhang .................. B01L 3/5027
506/2

* cited by examiner

*Primary Examiner* — Teresa E Strzelecka
(74) *Attorney, Agent, or Firm* — Brown Rudnick LLP; Thomas C. Meyers

(57) ABSTRACT

The invention generally relates to methods for distinguishing a rare genetic variation in a nucleic acid sequence.

23 Claims, 14 Drawing Sheets

$L_{nf}$ or $L_{nr}$ : Loci specific forward or reverse primer for target n
$P_n$ : Tag to ID the pool
$V_n$ : Variable Tag to ID the original nucleic acid target
$U_A$ or $U_B$ : Universal portion

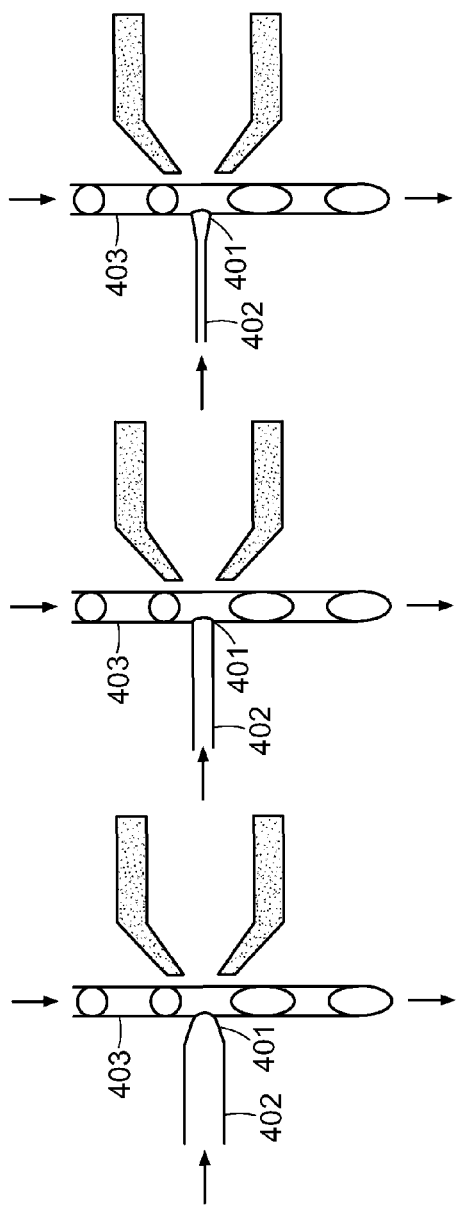
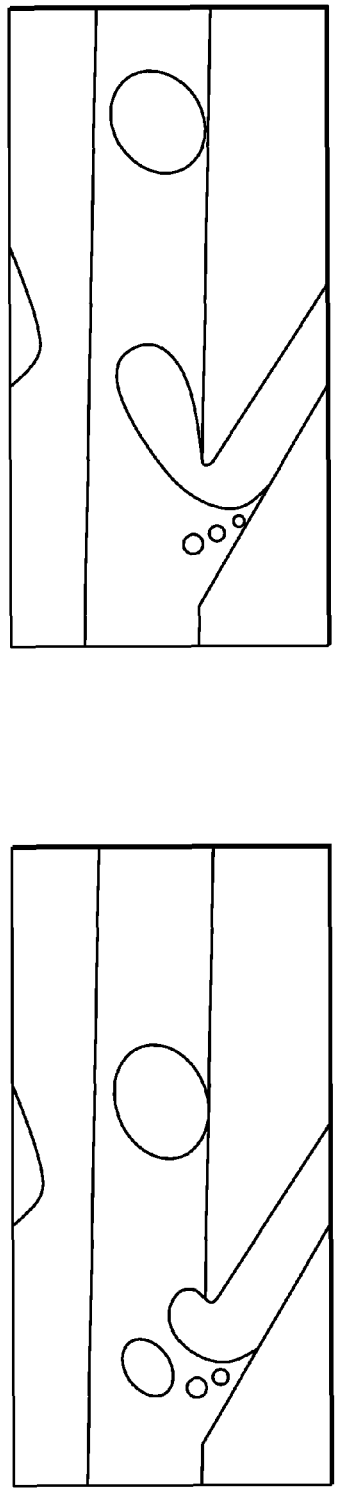

$L_{nf}$ or $L_{nr}$ : Loci specific forward or reverse primer for target n
$P_n$ : Tag to ID the pool
$V_n$ : Variable Tag to ID the original nucleic acid target
$U_A$ or $U_B$ : Universal portion

DISTINGUISHING RARE VARIATIONS IN A NUCLEIC ACID SEQUENCE FROM A SAMPLE

RELATED APPLICATIONS

The present application claims the benefit of and claims priority to U.S. Provisional Application Ser. No. 61/915,435 filed Dec. 12, 2013, the content of which is incorporated by reference herein in its entirety.

FIELD OF THE INVENTION

The invention generally relates to methods for distinguishing rare genetic variation in a nucleic acid sample.

BACKGROUND

Genetic variation underlies many aspects of disease, and their measurement is important to several fields of research. For example, counting de novo variation in humans, not present in their parents, has led to new insights into the rate at which our species can evolve. Counting genetic or epigenetic changes in tumors can inform fundamental issues in cancer biology. Variations lie at the core of current problems in managing patients with viral diseases such as AIDS and hepatitis by virtue of the drug resistance they can cause. Detection of donor DNA in the blood of organ transplant patients is an important indicator of graft rejection and detection of fetal DNA in maternal plasma can be used for prenatal diagnosis in a noninvasive fashion. In neoplastic diseases, which are all driven by somatic variation, the applications of rare variant detection are manifold; they can be used to help identify residual disease at surgical margins or in lymph nodes, to follow the course of therapy when assessed in plasma, and to identify patients with early, surgically curable disease when evaluated in stool, sputum, plasma, and other bodily fluids.

There is a distinct advantage in the ability to detect variation associated with a disease or condition that occurs at a very low frequency, such as in the case of cancer where the early stages which are most treatable have only a very low frequency of variation that could be detected in a sample (e.g. tissue biopsy or liquid biopsy such as from a blood draw). That problem is further enhanced when dealing with degraded nucleic acid in samples, such as nucleic acid found in formalin-fixed, paraffin-embedded (FFPE) tissue. In those samples, variation that exists at a low frequency in the original sample may have its numbers further reduced via degradation resulting in an even fewer copies of the nucleic acid available for detection.

Methods of sequencing and identifying genetic variations in samples are becoming commonplace. However, standard sequencing approaches are not ideally suited to detect rare variants due to the limits of detection associated with available sequencing platforms. Rare variants can occur at a rate that is lower than the limits of detection of a sequencing platform that may be a rate of occurrence of <=1% in a sample, where sequencing platforms typically have an accuracy rate that is no greater than about 99% even considering that many platforms require significant bioinformatics correction to achieve such accuracy. Thus it is generally appreciated that for rare variants that occur at less than 1%, there is a strong likelihood that the variation is either not identified or is identified but cannot be distinguished from experimental error and background noise of the system.

SUMMARY

The invention provides methods for distinguishing a genetic variation in a nucleic acid sequence from a false positive, such as a variation that occurs at a very low frequency in a sample. In the embodiments described herein the variation may include any type of nucleic acid variation known in the art such as small nucleotide polymorphism such as insertions and deletions (or combinations thereof also referred to as "indels"), structural variation (e.g. translocation, duplication, inversion, etc.). Aspects of the invention use molecular labeling, amplification, and multiplexing to identify individual nucleic acid molecules in a strand specific manner for sequencing. The invention provides two levels of quality control and confirmation of identified variation using sequencing technology. First, embodiments of the invention confirm that identified variation derives from molecules from the sample and are not an experimental artifact from sample preparation and/or sequencing process (e.g. polymerase error associated with amplification or sequencing). Second, embodiments of the invention are able to determine whether variation is present on both strands of a double stranded nucleic acid molecule, and thus are not just damage to the nucleic acid at the same location on the same strand, which is a common problem when working with degraded nucleic acid, such as found in formalin-fixed (FFPE) samples. In that manner, methods of the invention remove anomalies to improve the fidelity of calling variation and reduction of false positives.

Some embodiments of the invention include splitting the sample into two or more pools. Not all of the target loci need to be in each pool. In the described embodiments, the nucleic acid molecules in each pool are linearly amplified with a construct comprising a primer region recognizing at least one of the loci, a universal portion, a pool ID portion, and a unique sequence tag that comprises a sequence composition with a degree of variation that makes it unlikely that a particular sequence composition would occur more than once. The degree of variation may include a completely random sequence composition, a semi-random sequence composition (e.g. that may be result of combing short segments of sequence that may be known in a random fashion, see for example U.S. patent application Ser. No. 13/398,677, filed Feb. 16, 2012, which is hereby incorporated by reference herein in its entirety for all purposes) or known sequence composition that may be computed to enable identification and/or correction of introduced error (e.g. amplification or sequencing error). It will also be appreciated that the sequence composition of the unique sequence tag does not need to be known a priori but only needs to be easily distinguishable from the other members of the group of unique sequence tags used. In embodiments where the sequence composition is not known, it is important to know the sequence composition of the immediately adjacent element(s) so that it is clear from a sequence read where the boundaries of the unique sequence tag are for interpretation and correlation.

Each pool may include either a forward or a reverse primer construct specific to at least one loci, although some embodiments may include pools having some combination of forward and reverse primer constructs targeting the same or different loci (e.g. in equal or asymmetric abundances).

It will also be appreciated that in some embodiments, where target specificity is not required, the constructs may not need the primer region recognizing a target loci and the remaining components of the construct (e.g. pool ID, unique sequence tag, and universal portion) may be ligated to the end of a sample nucleic acid molecule for the linear amplification that employs a primer that recognizes some element of the construct. The ligation may be a double stranded ligation (e.g. sticky or blunt end) where in some instances the strands may be separated prior to the linear amplification step. The ligation may also be a single stranded ligation.

In a subsequent step, the linearly amplified molecules are compartmentalized into partitions such that the majority of partitions contain a single linearly amplified molecule that comprises the pool ID portion and the unique sequence tag that was derived from a strand of a single starting molecule. An amplification reaction is conducted in the compartmentalized partitions which could be an exponential amplification process (e.g. PCR or isothermal process such as LAMP or RPA) or a second linear amplification to produce clonal population of substantially identical copies of the of the original linear amplicon in each partition that includes copies of the unique sequence tag.

In some embodiments, the products of the amplification, including the unique sequence tag, are subject to another amplification reaction which may be a bulk exponential amplification reaction (e.g. PCR) to incorporate sequencing adaptors and sample indexes onto the ends of the second amplicons. The products from this amplification are then prepared and sequenced using any of the available sample preparation and sequencing technologies.

After sequencing, the sequence reads are analyzed to correlate sequence reads having the same unique sequence tag composition. Importantly, this is useful to identify and verify that molecules having sequence variation do not result from an experimental artifact, where multiple sequence reads having the same unique sequence tag composition and same variation are understood to have originated from the same single stranded molecule in the sample. Additionally, the sequence reads are analyzed to confirm that the same variation is found on both the forward and reverse strands. Variation found in sequence reads from complementary forward and reverse strands (e.g. having complementary Watson-Crick base pair associations) are aligned and correlated where multiple sequence reads from that the forward strand correlate to a first unique sequence tag and multiple sequence reads from that the reverse strand correlate to a second unique sequence tag is further confirmation that the variation is real and not an artifact. Variation found that does not correlate well with sequence composition from sequence reads (e.g. some proportion of sequence reads have the variation and the remainder do not) that correlate with the same unique sequence tags are called as false positives, likely a result of some artifact from the sample, or preparation/sequencing process.

As described above, certain embodiments of the invention involve splitting a sample including nucleic acid molecules into at least two pools and linearly amplifying one or more loci from a forward strand of the nucleic acid molecules in the first pool and the same one or more loci from a reverse strand in the second pool to generate forward strand amplification products and reverse strand amplification products. The linear amplification employs primer constructs comprising a target specific primer region, a first tag region that identifies the pool with known sequence composition (e.g. the first pool, the second pool, etc.), a second tag region comprising variable sequence composition (e.g. the unique sequence tag referred to above), and a universal region used as a primer recognition site in subsequent process steps. The variable sequence composition of the second tag region comprises a length and composition such that the likelihood that any two linear amplifications would have the same sequence composition is extremely low or non-existent.

As a result of the linear amplification process and the design of the primers used, the forward strand amplification products comprise multiple copies of the target locus from a single molecule (e.g. from the forward strand of the double stranded molecule) each with a copy of the same unique sequence tag. Similarly, the reverse strand amplification products typically comprise multiple copies of the target locus from a single molecule (e.g. from the reverse strand of the single double stranded molecule) each with a copy of the same unique sequence tags that are different than the unique sequence tags in the forward strand amplification products. It will, however, also be appreciated that the linear amplification may include a single round of strand extension producing only a single copy with the unique sequence tag from either the forward or reverse strands or both. It is important to note that each primer construct used in any pool of the linear amplification has a different unique sequence tag, even constructs comprising the same target specific primer region and/or first tag region. Further, multiplexed primer constructs may be used in the same pool where there are primer constructs have target specific primer regions specific for different loci, but the same first tag region that is specific to the pool.

The forward and reverse strand amplification products are compartmentalized into partitions in a manner in which a plurality of the partitions comprise only a single forward strand amplification product or a single reverse strand amplification product. The forward and reverse strand amplification products are amplified in the compartmentalized portions to further increase copy numbers to produce a clonal population having substantially identical sequence composition. As described above, the amplification may be exponential. Exemplary compartmentalizing techniques are shown for example in, Griffiths et al. (U.S. Pat. No. 7,968,287) and Link et al. (U.S. patent application number 2008/0014589), the content of each of which is incorporated by reference herein in its entirety. In certain embodiments, the compartmentalizing involves forming droplets and the compartmentalized portions are the droplets. An exemplary method involves for forming droplets involves flowing a stream of sample fluid including the amplicons such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil, particularly, a fluorinated oil. In certain embodiments, the carrier fluid includes a surfactant, such as a fluorosurfactant. The droplets may be flowed through channels.

Subsequently, in some embodiments the amplification products are pooled into a combined mixture and subject to another amplification process that further increase copy number but also employs primer constructs that incorporates sample specific index sequences (e.g. also referred to as "barcode sequences" or "multiplex identifiers") and adaptor sequence elements that may be specific to a particular sequencing platform for the sequencing process.

The products from the second (e.g. bulk) amplification step are sequenced to produce sequence reads. The sequence reads are analyzed to determine that a same variation is found on both the forward and reverse strands of the nucleic acid molecules. Additionally, the unique sequence tag portion in the sequence reads is analyzed to determine that the same variation is found in multiple different nucleic acid molecules. A variation found on the forward and reverse strands that are also found on in multiple different nucleic acid molecules is a true variation. Sequencing may be by any method known in the art. Sequencing-by-synthesis is a common technique used in next generation procedures and works well with the instant invention. However, other sequencing methods can be used, including sequence-by-ligation, sequencing-by-hybridization; gel-based techniques and others. In general, sequencing involves hybridizing a primer to a template to form a template/primer duplex, contacting the duplex with a polymerase in the presence of a detectably-labeled nucleotides under conditions that permit the polymerase to add nucleotides to the primer in a template-dependent manner. Signal from the detectable label is then used as to identify the incorporated base and the steps are sequentially repeated in order to determine the linear order of nucleotides in the template. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes.

In the same or alternative embodiments, the first amplification step to incorporate the unique sequence tag may include the production of a concatemerized product from a single nucleic acid, where the product comprises repeating sequence composition that includes a copy of a target locus and a unique sequence tag (with variable sequence composition as described above). In the described embodiments, a variable barcode construct may be constructed and arranged for ligation to both ends of the individual sample nucleic acid molecules in order to circularize. In some embodiments, the nucleic acid molecules may be sheared to a desired length using techniques known in the art (e.g. restriction enzyme digestion, sonication, etc.) and may be modified to improve ligation efficiency. One example of such a modification includes what is referred to as "A tailing" that comprises adding an Adenine nucleotide to the 3' ends of the nucleic acid strands (e.g. via Taq DNA Polymerase) which improves the likelihood that only a single sample nucleic acid molecule will ligate to the variable barcode construct as opposed to multiple sample nucleic acid molecules ligating to each other which can happen with blunt end ligation.

In the described embodiments, the variable barcode construct comprises a region comprising variable sequence composition (e.g. unique sequence tag). As described above, in some embodiments the sequence composition of the unique sequence tag is not known a priori, and may be flanked on one or both sides by a region of known sequence composition (e.g. anchor sequence tag). The anchor sequence tag is useful during analysis of the sequence composition because the sequence is known, thus the ends of the unique sequence tag can easily be identified. However, it will be appreciated that in some embodiments the sequence composition of the unique sequence tag may be known, and in some cases computed to be easily distinguishable even if errors are introduced, where anchor sequence tags may not be necessary to identify the complete unique sequence tag.

After ligation, an amplification is performed on the circularized nucleic acid molecules that include the ligated random barcode construct using what is referred to as rolling circle amplification (referred to as RCA). The RCA process uses a target specific primer that hybridizes to a complementary sequence on the circularized molecule and a polymerase (e.g. typically phi29 DNA polymerase) synthesizes a strand of DNA as it repeatedly reads around the circularized template. The result is a linearly amplified product that comprises a single strand concatemer of the target loci and the random barcode construct.

Also, the concatemer would typically include forward and reverse target sites for primers used in a subsequent amplification step, which may be an exponential or linear amplification as described above. In some embodiments, the single molecule concatemer product is compartmentalized and amplified as described above. The amplification products from the second amplification may then subject to a bulk exponential amplification and sequencing steps as described above.

Methods of the invention are useful when analyzing samples for rare variation, such as abnormal nucleic acids that include variation associated with diseases, such as cancer or recurrence of cancer. Methods of the invention are also useful when analyzing mixed samples to look for a specific target within the mixed sample, such a fetal nucleic acid in maternal blood, or a nucleic acid from a transplanted organ. Methods of the invention are also useful when analyzing samples that include degraded nucleic acid, such as formalin-fixed, paraffin-embedded tissue or ancient samples.

BRIEF DESCRIPTION OF THE DRAWINGS

FIG. 3A shows a non-perpendicular orientation of the two channels at the merge site. FIGS. 3B-3E show a perpendicular orientation of the two channels at the merge site.

FIG. 4 also shows that an insulating layer may optionally be placed between the channels and the electrodes.

FIG. 7A is with electrodes and FIG. 7B is without electrodes.

FIG. 9 shows an embodiment that employs an electric field to facilitate droplet merging.

FIGS. 11A-11C show embodiments in which the size of the orifice at the merge point for the channel through which the second sample fluid flows may be the smaller, the same size as, or larger than the cross-sectional dimension of the channel through which the immiscible carrier fluid flows.

FIGS. 12A-12B show a set of photographs showing an arrangement that was employed to form a mixed droplet in which a droplet of a first fluid was brought into contact with a bolus of a second sample fluid stream, in which the bolus was segmented from the second fluid stream and merged with the droplet to form a mixed droplet in an immiscible carrier fluid. FIG. 12A shows the droplet approaching the growing bolus of the second fluid stream. FIG. 12B shows the droplet 25 merging and mixing with the bolus of the second fluid stream.

DETAILED DESCRIPTION

Figure 1A:
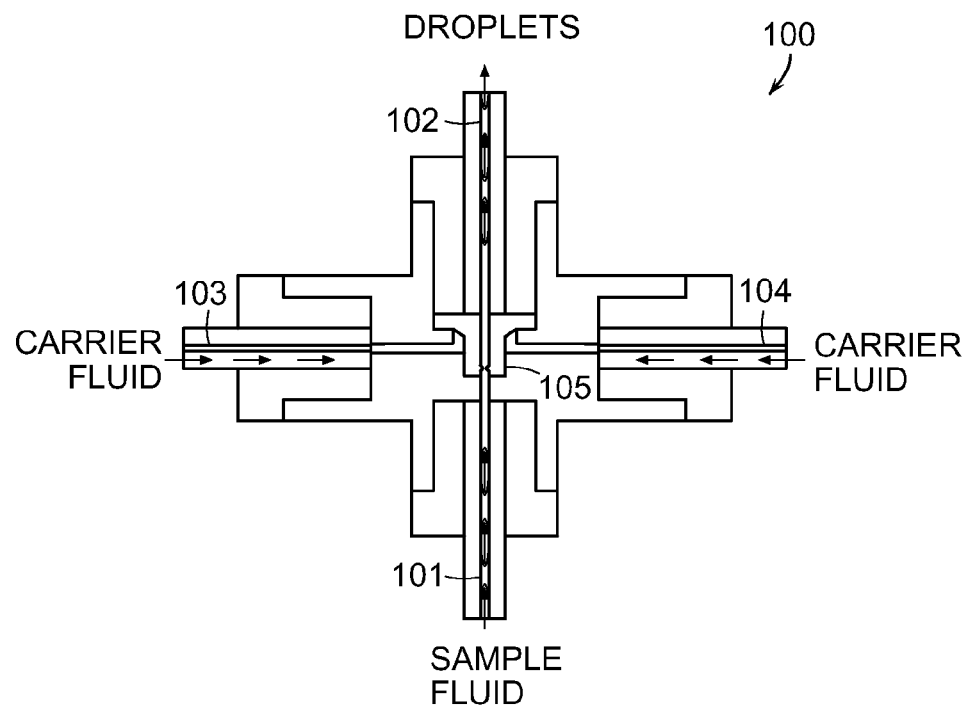
FIGS. 1A-1B show an exemplary embodiment of a device for droplet formation.

The invention generally relates to methods for distinguishing genetic variation that occurs at a very low frequency in a in a sample, particularly a frequency that is below the limits of detection of sequencing platforms. Embodiments of the invention may involve splitting the sample into two or more pools and using linear amplification and primers to create forward and reverse strand products of a nucleic acid comprising a target locus. In one embodiment only one of either the forward or the reverse primer for a given loci in a given pool, but in some cases it may be advantageous to have both primers present in one or more pools in equal or asymmetric abundances.

In an exemplary embodiment, the constructs include a target loci specific primer portion at the 3' end and a universal portion at the 5'end. A variable tag (unique sequence tag) and primer pool tag can be in any order after the loci specific and before the universal. In some cases it is possible to use the difference in sequence composition between the universal portions of each primer as indicative of the primer pool tag. After the addition of the primers, the nucleic acids in the pools undergo linear amplification. In an alternative embodiment the constructs include a universal portion at the 5' end, with a variable tag (unique sequence tag) and a primer pool tag that is ligated to the nucleic acids. Similarly the ligated construct-nucleic acid complexes in the pools are subject to linear amplification using a primer that recognizes the universal portion. In either embodiment, the linear amplification is performed by using only a forward construct or a reverse construct in a pool, where for instance there is no primer that initiates extension from the first strand product. In other words, each round of amplification creates a single copy from the original sample nucleic acid template but does not copy newly synthesized strands. This is also the case in pools that include both forward and reverse constructs where there is no primer in the pool that amplifies the first strand product from any construct.

In certain embodiments, the method involves a step of including the compliment to the universal portion; and the forward or reverse primer that was not present in the linear amplification step with the products of the linear amplification in partitions. In some embodiments, the partitions include aqueous droplets comprising a small volume (e.g. picoliter-nanoliter volumes such as a volume of about 5 pico-liters). The contents of the compartments are subjected to an amplification reaction to produce amplicons that are multiply labeled with a variable ID (unique sequence tag) that identifies a starting molecule, a pool ID, and a Universal primer end.

There is another optional step to clean-up the PCR reaction and to incorporate sequencing adaptors and sample indexes onto the ends of the amplicons. Next, the PCR products are sequenced, for instance by using a massively parallel sequencing by synthesis approach. However, any other technique would be sufficient provided that the bases of interest are read multiple times, allowing for low prevalence variation or other impurities to be identified with high fidelity (low false positives). The sequence reads are analyzed to determine that a same variation is identified, and is desirable if found on both the forward and reverse strands of the nucleic acid molecules. Additionally, the unique sequence tag portion in the sequence reads is analyzed to determine that the same variation is found in multiple different nucleic acid molecules. A variation found on the forward and reverse strands that is also found on multiple different nucleic acid molecules is considered a true variant.

Target

Nucleic acid generally is acquired from a sample taken from an organism or synthesized. Target molecules for labeling and/or detection according to the methods of the invention include, but are not limited to, genetic and proteomic material, such as DNA, RNA, cDNA, PNA, LNA. Methods of the invention are applicable to DNA from whole cells or to portions of genetic or proteomic material obtained from one or more cells. For a patient, the sample may be obtained in any clinically acceptable manner, and the nucleic acid templates are extracted from the sample by methods known in the art. Nucleic acid templates can be obtained as described in U.S. Patent Application Publication Number US2002/0190663 A1, published Oct. 9, 2003. Generally, nucleic acid can be extracted from a biological sample by a variety of techniques such as those described by Maniatis, et al. (Molecular Cloning: A Laboratory Manual, Cold Spring Harbor, N.Y., pp. 280-281, 1982), the contents of which are incorporated by reference herein in their entirety.

Nucleic acid templates include deoxyribonucleic acid (DNA) and/or ribonucleic acid (RNA). Nucleic acid templates can be synthetic or derived from naturally occurring sources. In one embodiment, nucleic acid templates are isolated from a biological sample containing a variety of other components, such as proteins, lipids and non-template nucleic acids. Nucleic acid templates can be obtained from any cellular material, obtained from an animal, plant, bacterium, fungus, or any other cellular organism. Biological samples for use in the present invention include viral particles or preparations. Nucleic acid may also be acquired from a microorganism, such as a bacteria or fungus, from a sample, such as an environmental sample. Nucleic acid templates can be obtained directly from an organism or from a biological sample obtained from an organism, e.g., from blood, urine, cerebrospinal fluid, seminal fluid, saliva, sputum, stool and tissue. In a some embodiments, nucleic acid may be obtained from fresh frozen plasma (FFP), or formalin-fixed, paraffin-embedded (FFPE) tissues. Any tissue or body fluid specimen may be used as a source for nucleic acid for use in the invention. Nucleic acid templates can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton X series (Triton X-100 t-Oct-C6H4-(OCH2-CH2)xOH, x=9-10, Triton X-100R, Triton® X-114 x=7-8), octyl glucoside, polyoxyethylene(9)dodecyl ether, digitonin, IGEPAL CA630 octylphenyl polyethylene glycol, n-octyl-beta-D-glucopyranoside (betaOG), n-dodecyl-beta, Tween 20 polyethylene glycol sorbitan monolaurate, Tween 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl) dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), beta.-mercaptoethanol, DTE, GSH, cysteine, cysteamine, tricarboxyethyl phosphine (TCEP), or salts of sulfurous acid. Once obtained, the nucleic acid is denatured by any method known in the art to produce single stranded nucleic acid templates and a pair of first and second oligonucleotides is hybridized to the single stranded nucleic acid template such that the first and second oligonucleotides flank a target region on the template.

In certain embodiments, the nucleic acid molecules are bound as to other target molecules such as proteins, enzymes, substrates, antibodies, binding agents, beads, small molecules, peptides, or any other molecule and serve as a surrogate for quantifying and/or detecting the target molecule. Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures). Proteins or portions of proteins (amino acid polymers) that can bind to high affinity binding moieties, such as antibodies or aptamers, are target molecules for oligonucleotide labeling, for example, in droplets.

Formation of Pools and Amplification

Figures 13, 14:
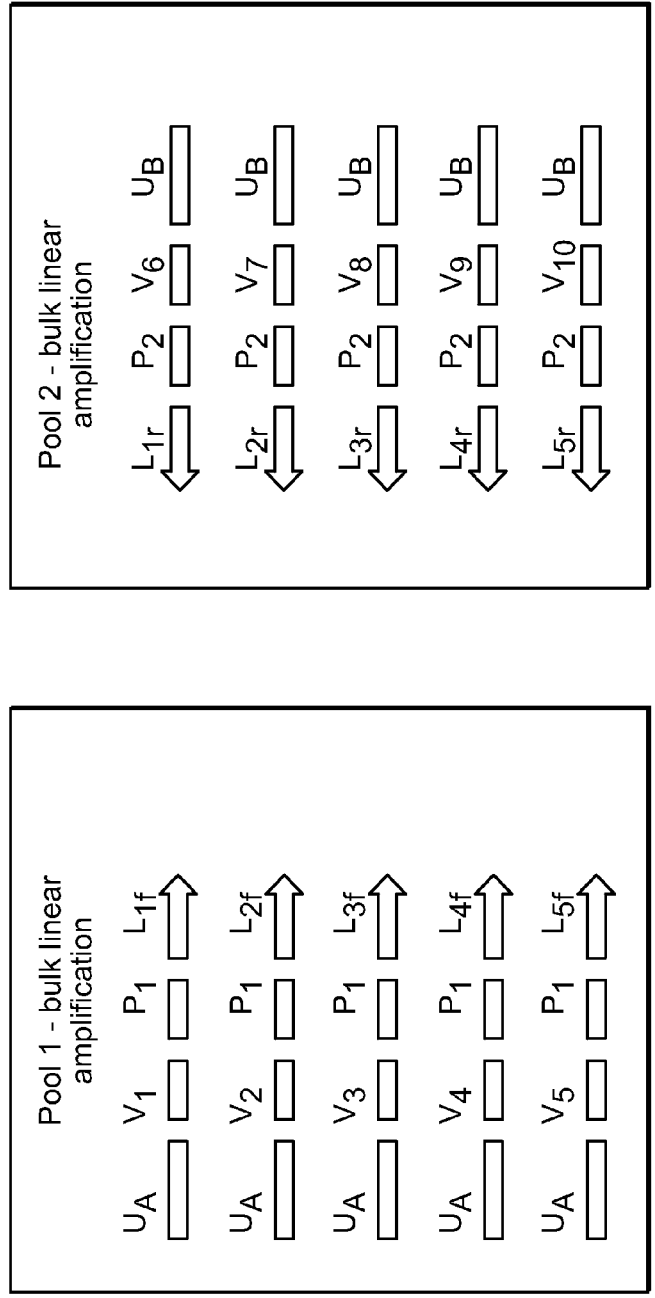
FIG. 13 provides an illustrative example of a primer construct useful for linear amplification containing the loci specific forward (or reverse primer), a sequence tag to identify the pool, a variable tag to identify the reaction (e.g. a unique sequence tag), and a universal portion useful as a primer recognition site.
FIG. 14 provides an illustrative example of the primer constructs of FIG. 13 in a first pool comprising forward strand constructs targeting different loci and a second pool comprising reverse strand constructs targeting the different loci.

In some embodiments of the presently described invention, a sample containing one or more target loci is split into two or more pools, or aliquots. In some embodiments it may not be necessary for all of the loci of interest to be present in each pool, however in most embodiments it is typically desirable. In one embodiment, primer constructs are added to each pool for linear amplification, such as for example a construct comprising an arrangement of components as illustrated in FIG. 13 that includes a universal portion comprising known sequence composition that in is some embodiments is distinctive from naturally occurring sequence composition; a unique sequence tag comprising sequence composition with a sufficient degree of variation from all other unique sequence tags to specifically identify the original nucleic acid target, a tag to identify the pool, and either the forward or reverse primer region that specifically recognizes a target of interest. In some embodiments, there are a greater number of unique sequence tags than the number of linear amplification products, such that there is no possibility of having products that include a unique sequence tag with identical sequence composition. In the embodiments described herein, the unique sequence tags may include a length (e.g. number of sequence positions) required to randomly generate or compute sequence composition for the unique sequence tags that satisfy the requirement for complete uniqueness.

In the described embodiments the universal portion should be positioned at the 5' end of the construct with extension from 3' end of the primer region so that the full construct is operably connected to the linear amplification product. In the described embodiments the universal portion is employed as a target site for another primer species used in later amplification and/or sequencing steps and thus it is important that it is positioned as the 5' most element in the construct. Further, while the tag that identifies the pool may be useful in many circumstances it is not absolutely necessary for the operation of the invention. In the presently described embodiment, the construct is typically single stranded, however in some embodiments the construct may be partially double stranded where the primer region is single stranded and one or more of the other components is double stranded.

In embodiments of the presently described invention, a sample containing one or more target loci is divided into two pools as illustrated in the example of FIG. 14. For instance, FIG. 14 shows a plurality of constructs using the structure illustrated in FIG. 13 in a first pool where each construct has a different loci specific forward primer, a different variable tag (e.g. unique sequence tag), the same tag that identifies the first pool, and the same universal portion. FIG. 14 also shows a second pool with a plurality of constructs where each construct has a different loci specific reverse primer, a different variable tag (e.g. unique sequence tag), the same tag that identifies the second pool, and the same universal portion which may be the same or different than the universal portion used for the first pool (e.g. $U_A$ and $U_B$ may be the same or different from each other). In the presently described example, the sample may include genomic DNA having some number of genomic equivalents so that when divided equally each pool has a sufficient representation to the target loci of interest. It is important to note that the unique sequence tags used in the first and second pools are all unique from each other in composition such that they become specifically associated with a single nucleic acid in the sample as a result of the linear amplification (e.g. illustrated in FIG. 14 as $V_1$-$V_{10}$).

In an alternative embodiment where target specificity is not required, a construct similar to the one illustrated in FIG. 13 may be employed but differs in that there is no primer region. In the described embodiment the construct may be ligated to the end of the target using the end of the tag to identify the pool or the unique sequence tag (e.g. on either a forward or reverse strand). The linear amplification may then use a primer species that recognizes the universal portion, as described above, to produce a linear amplification product comprising the complete construct operably connected to the linear amplification product of the nucleic acid. In the presently described embodiment it may not be necessary to split the sample into different pools so long as there is no primer present that will amplify the first strand product, but is important to note that the unique sequence tags used are all unique from each other in composition such that they become specifically associated with a single nucleic acid in the sample as a result of the ligation and linear amplification. Those of ordinary skill in the related art will appreciate that any type of ligation may be used and that the construct may be double stranded for the ligation (e.g. for sticky end or blunt end ligation), partially double stranded (e.g. with a single stranded portion), or single stranded.

In the described embodiments, a linear amplification reaction is carried out in each pool by, for example, using only a one member of a pair of primer species so that a first strand product is produced but no copies of the first strand product are produced. Linear amplification is well known in the art, an example of which may be found in "DNA linear amplification," Chih Long Liu, Bradley E. Bernstein and Stuart L. Schreiber, Department of Chemistry and Chemical Biology, Harvard University, 12 Oxford St., Cambridge, Mass., 02138, USA.

Figure 15:
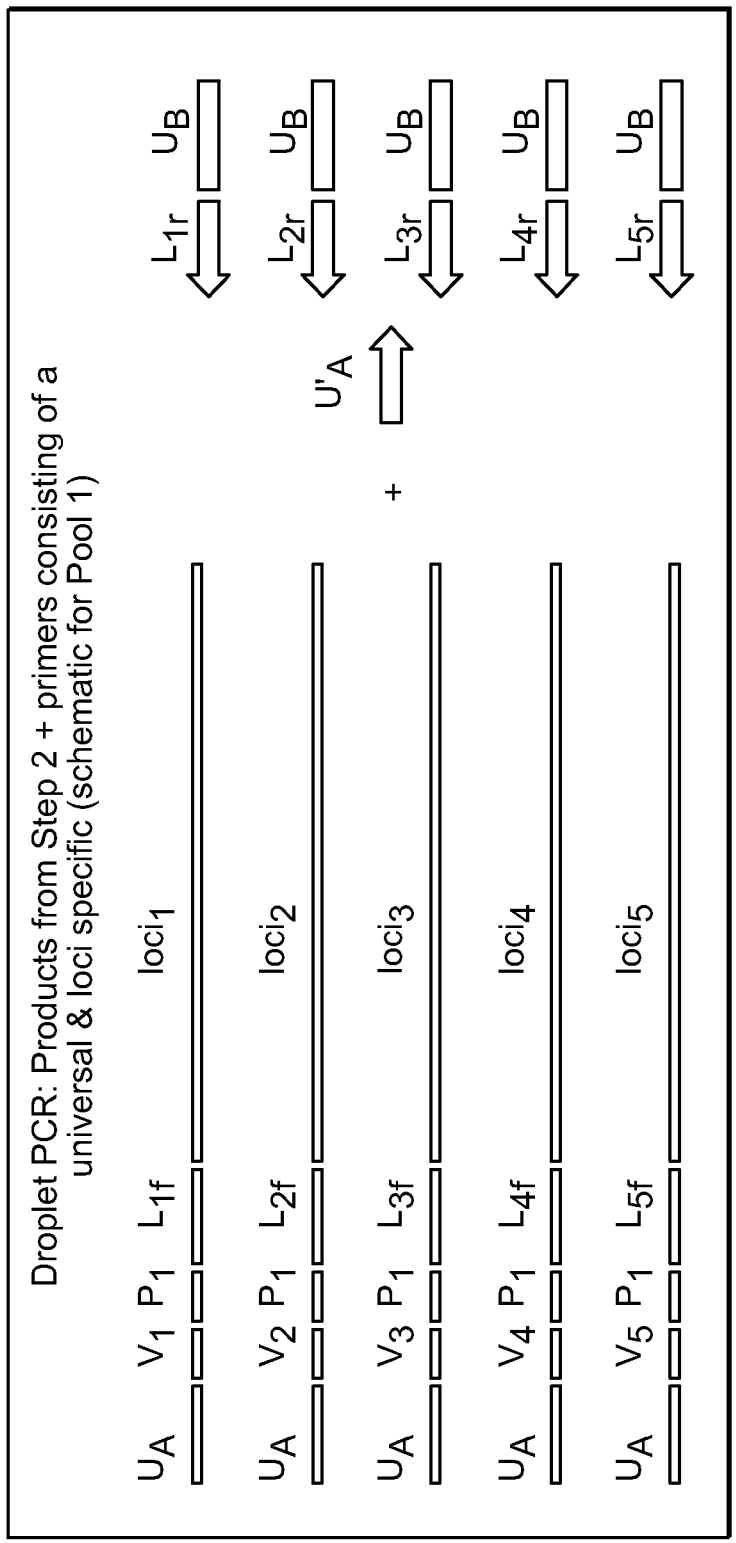
FIG. 15 provides an illustrative example of linear amplification products from the first pool of FIG. 14 combined with primers recognizing the universal portion on the product and loci specific constructs the produce an exponential amplification product comprising the sequence tag, the random tag, and two universal portions (e.g. one at each end of the products).

At the conclusion of the linear amplification step, each pool has a plurality of first strand amplicons for each of the specific loci targeted or ligated nucleic acid. For example, as shown in FIG. 15, the products of a linear amplification performed in the first pool of FIG. 14 is illustrated and includes a first strand copy of the loci targeted coupled to the tag identifying the pool, a unique variable tag for each amplicon and the universal portion. Those of ordinary skill in the related art will appreciate that the linear amplification process may include multiple rounds of cycling where each cycle produces a first strand product from a template. Alternatively, the linear amplification may include only a single round that produces a single copy of the nucleic acid and unique sequence tag. For embodiments using a loci specific primer, each construct includes a different unique sequence tag and thus each first strand product will have a different unique sequence tag even if the same original template was amplified in different rounds.

In some embodiments, the linear amplification products from the pools may be combined together or maintained separately.

Figure 16:
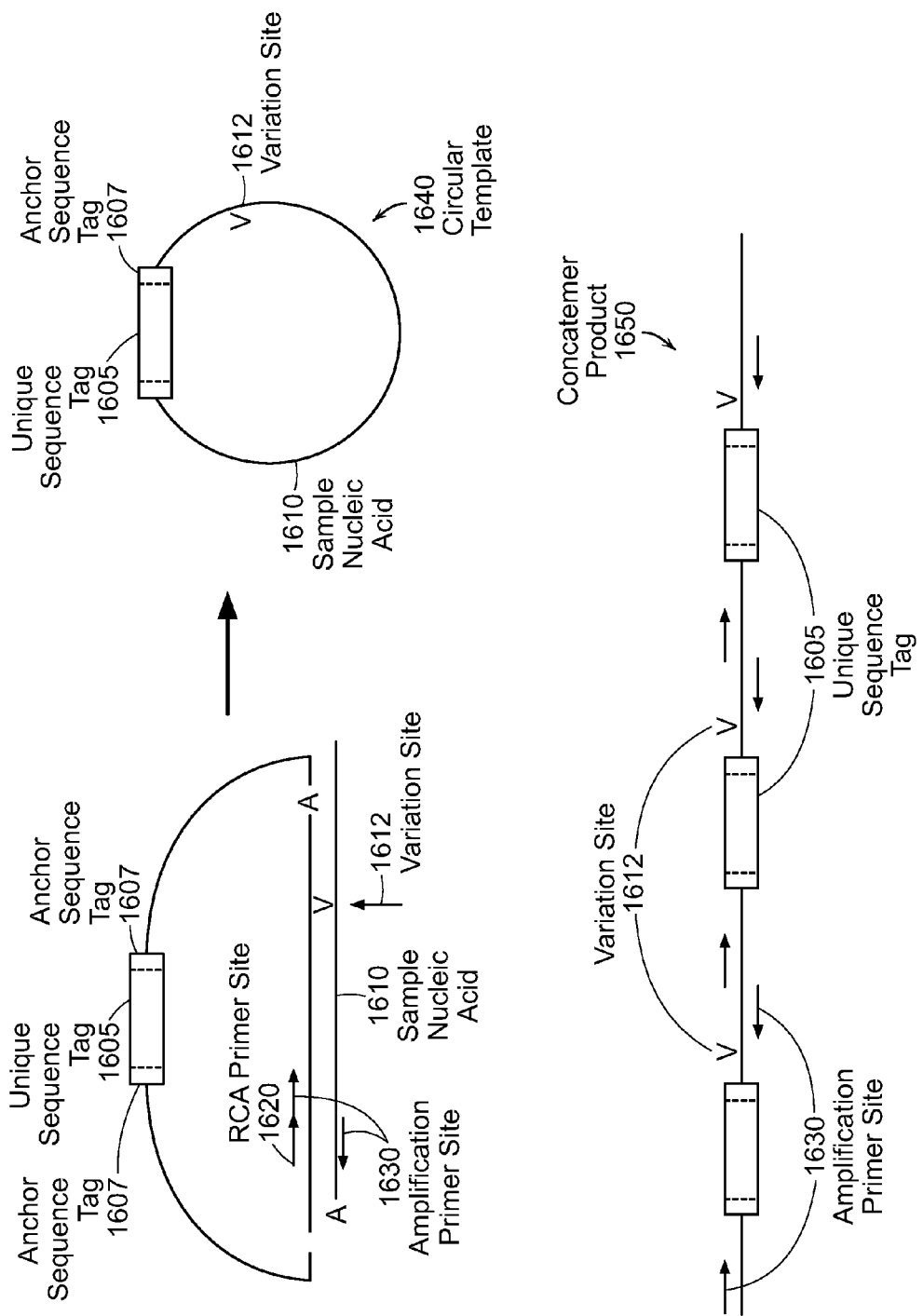
FIG. 16 is an illustrative example of an approach to producing a concatemer comprising a plurality of copies of a unique sequence tag and a sequence variation.

In yet another embodiment of the invention, a unique sequence tag may be incorporated with a nucleic acid sequence that may comprise a variant of interest into a concatemer product by linear amplification of a circularized template. FIG. 16 provides an illustrative example of an approach where both ends unique sequence tag 1605 are ligated to both ends of sample nucleic acid 1610 that creates circular template 1640. In some embodiments, the nucleic acid molecules may be sheared to a desired length using techniques known in the art (e.g. restriction enzyme digestion, sonication, etc.) and may be modified to improve ligation efficiency. One example of such a modification includes what is referred to as "A tailing" that comprises adding an Adenine nucleotide to the 3' ends of the nucleic acid strands (e.g. via Taq DNA Polymerase) which improves the likelihood that only a single sample nucleic acid molecule will ligate to unique sequence tag 1610 as opposed to multiple sample nucleic acid molecules ligating to each other which can happen with blunt end ligation.

Unique sequence tag 1610 comprises a region comprising variable sequence composition as described above in other embodiments. As described above, in some embodiments the sequence composition of unique sequence tag 1610 is not known a priori, and may be flanked on one or both sides by anchor sequence tag 1607 comprising known and easily identifiable sequence composition immediately adjacent to tag 1610. Anchor sequence tag 1607 is useful during analysis of the sequence composition because the sequence is known, thus the ends of the unique sequence tag can easily be identified. However, it will be appreciated that in some embodiments the sequence composition of the unique sequence tag may be known, and in some cases computed to be easily distinguishable even if errors are introduced, where anchor sequence tags 1607 may not be necessary to identify the complete unique sequence tag.

After ligation has produced circular template 1640, an amplification reaction is performed using, for example, what is referred to as rolling circle amplification (also referred to as RCA). The RCA process uses a target specific primer that hybridizes to RCA primer site 1620 on the circularized molecule and a polymerase (e.g. typically phi29 DNA polymerase) synthesizes a strand of DNA as it repeatedly reads around the circularized template for a duration that produces concatemer product 1650 that comprises a desired number of repeats (displacing the primer and synthesized molecule from the template as it passes). In the present example, concatemer product 1650 comprises a single strand comprising a repeating segment of sample nucleic acid 1610, unique sequence tag 1605 and may include anchor sequence tag 1607 and/or variation site 1612. It will be appreciated that the repeats of unique sequence tag 1605 in concatemer product 1650 all have the same sequence composition.

Also, the concatemer product 1650 comprises primer sites 1630 for primers used in a subsequent amplification step, which may be an exponential or linear amplification as described above. For example, primer sites 1630 are arranged in what may be referred to as an "outie" relationship on original sample nucleic acid 1610 (e.g. the 3' end oriented away from primer partner as opposed to oriented towards the primer partner), where the circularization and linear amplification produces the correct orientation of primer sites 1630 to produce amplification products that comprise a copy of unique sequence tag 1605 and variation site 1612.

It will also be appreciated that FIG. 16 is an illustrative representation not drawn to scale, and thus should not be considered as limiting. For instance prior to ligation unique sequence tag 1605 and anchor sequence tag 1607 appear to have additional sequence on either end. While it is certainly possible and may be desirable in some instances to have additional sequence to increase the length of insert relative to sample nucleic acid 1610, it is not required. In fact in some embodiments it is highly desirable to ligate sample nucleic acid 1610 directly to anchor sequence tag 1607 or unique sequence tag 1605 (in embodiments where anchor sequence tag 1607 is not included).

In the described embodiments, the single molecule concatemer product is compartmentalized and amplified as described above. The amplification products from the second amplification are then subject to a bulk exponential amplification and sequencing steps as described above.

It will be appreciated that the constructs described herein may be created using methods known to those of skill in the art including ligation of synthesized components or synthesis of complete constructs. Also primer species are commercially available, and are well known in the art. Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule ($Td=2(A+T)+4(G+C)$). Another method for determining the melting temperature of primers is the nearest neighbor method (SantaLucia, "A unified view of polymer, dumbbell, and oligonucleotide DNA nearest-neighbor thermodynamics", 1998, P.N.A.S., 95 (4): 1460-5). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAs is from Hitachi Software Engineering. The TM (melting or annealing temperature) of each primer is calculated using software programs such as Oligo Design, available from Invitrogen (a division of Life Technologies/Thermo Fisher Scientific).

Distribution into Partitions and Amplification

In the embodiments described herein it is highly desirable to distribute and compartmentalize the linear amplification products into partitions so that the partitions generally comprise one linear amplification product nucleic acid, or none. As described above the linear amplification products may be combined for partitioning or maintained separately to maintain the separation of the pools that may be desirable in some instances. In some embodiments, additional reagents may be added to the combined mixture or pools prior to partitioning or added post partitioning using methods described in greater detail below.

Exemplary compartmentalizing techniques are shown for example in, Griffiths et al. (U.S. Pat. No. 7,968,287) and Link et al. (U.S. patent application number 2008/0014589), the content of each of which is incorporated by reference herein in its entirety. In some embodiments, the compartmentalized portions are droplet based emulsion systems and compartmentalizing involves introducing the linear amplification products to a stream of droplets. Each droplet includes either the forward or reverse amplification product.

Figure 1B:
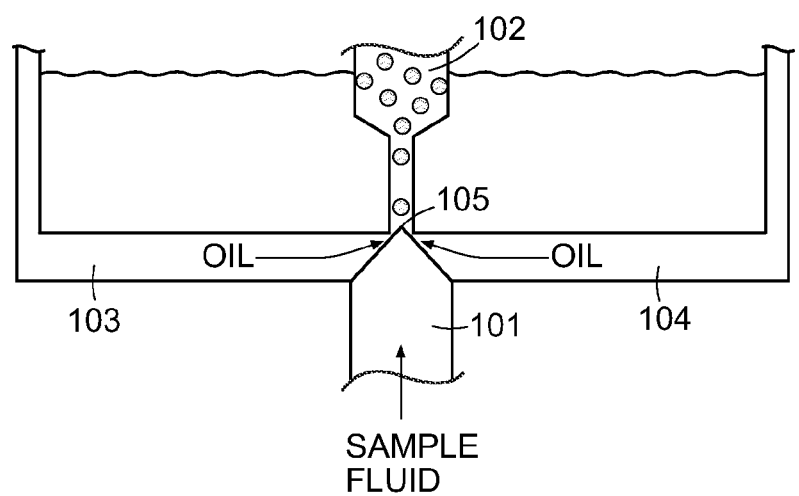

Sample droplets may be formed by any method known in the art. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to RainDance Technologies Inc. The content of each of which is incorporated by reference herein in its entirety. FIGS. 1A-1B show an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 1B). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

Typical embodiments of "emulsions" include creating a stable emulsion of two immiscible substances, and in the embodiments described herein generally refer to an emulsion of aqueous droplets in a continuous oil phase within which reactions may occur. In particular, the aqueous droplets of an emulsion amenable for use in methods for conducting reactions with biological samples and detecting products may include a first fluid, such as a water based fluid (typically referred to as "aqueous" fluid) suspended or dispersed as droplets (also referred to as a discontinuous phase) within another fluid, such as a hydrophobic fluid (also referred to as a continuous phase) that typically includes some type of oil. Examples of oil that may be employed include, but are not limited to, mineral oils, silicone based oils, fluorinated oils, partially fluorinated oils, or perfluorinated oils.

One example of an aqueous fluid compatible with embodiments of the invention may include an aqueous buffer solution, such as ultrapure water (e.g., 18 mega-ohm resistivity, obtained, for instance by column chromatography), 10 mM Tris HCl and 1 mM EDTA (TE) buffer, phosphate buffer saline (PBS) or acetate buffer. In the presently described example, any liquid or buffer that is physiologically compatible with nucleic acid molecules or encapsulated biological entity can be used. Also, in the same or alternative example a carrier fluid compatible with embodiments of the invention includes a non-polar solvent, decane (e g., tetradecane or hexadecane), fluorocarbon oil, silicone oil or another oil (for example, mineral oil). In certain embodiments, the carrier fluid may contain one or more additives, such as agents which increase, reduce, or otherwise create non-Newtonian surface tensions (surfactants) and/or stabilize droplets against spontaneous coalescence on contact.

Embodiments of surfactants that act to stabilize emulsions, which may be particularly useful for embodiments that include conducting reactions with biological samples such as PCR may include one or more of a silicone or fluorinated surfactant. For example, in microfluidic embodiments the addition of one or more surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils and substantially reduce the likelihood of droplet coalescence.

In some embodiments, the aqueous droplets may be coated with a surfactant or a mixture of surfactants, where those of skill in the art understand that surfactant molecules typically reside at the interface between immiscible fluids, and in some cases form micelles in the continuous phase when the concentration of surfactant(s) is greater than what is referred to as the critical micelle concentration (also sometimes referred to as CMC). Examples of surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethyleneglycol esters, etc.) and alkanolamines (e.g., diethanolamine-fatty acid condensates and isopropanolamine-fatty acid condensates). In certain embodiments, the carrier fluid may be caused to flow through the outlet channel so that the surfactant in the carrier fluid coats the channel walls. In one embodiment, the fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

Further, in some embodiments other reagents that act as droplet stabilizers (also referred to as passivating agents) may be included. Useful droplet stabilizing reagents may include, but are not limited to, polymers, proteins, BSA, spermine, or PEG.

Various methods of forming emulsions may be employed with the described embodiments. In the some embodiments methods involve forming aqueous droplets where some droplets contain zero target nucleic acid molecules, some droplets contain one target nucleic acid molecule, and some droplets may contain multiple target nucleic acid molecules. It will be appreciated by those of skill in the art that in some embodiments it may be desirable for individual droplets to contain multiple nucleic acid molecules from a sample, however in certain assays there may be a discrete number of targets of interest where droplets are generated based on the likelihood that there is at most a single target of interest in each droplet in the presence of other nucleic acid molecules that are not targets of interest.

In some embodiments the number of target nucleic acid molecules in the droplets is controlled via a limiting dilution of the target nucleic acid molecules in the aqueous solution. Alternatively, in some embodiments the number of target nucleic acid molecules in the droplets is controlled via a method of partitioning very small volumes of the aqueous fluid (e.g. picoliter-nanoliter volumes such as a volume of about 5 picoliters) into the droplet where the statistical likelihood of distributing multiple target nucleic acid molecules in the same droplet is very small. In some or all of the described embodiments, the distribution of molecules within droplets can be described by Poisson distribution. However, it will be appreciated that methods for non-Poisson loading of droplets may be employed in some embodiments and include, but are not limited to, active sorting of droplets such as by laser-induced fluorescence, or by passive one-to-one loading.

In certain embodiments, the linear amplification products are pooled and then reagents for amplification are subsequently introduced after droplet formation. In those embodiments, droplets with a single template per droplet are formed. For example, after formation of the droplets containing either the forward or reverse amplification product, the droplets are contacted with a flow of one or more sample fluid streams including reagents for amplification. Contact between the droplets and the fluid stream results in a portion of the fluid stream integrating with the droplets to form a mixed droplet. Each mixed droplet includes either forward or reverse amplification product and a plurality of amplicons.

Figure 2A:
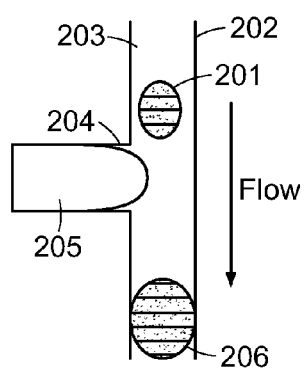
FIGS. 2A-2C show an exemplary embodiment of merging two sample fluids.
Figure 2B:
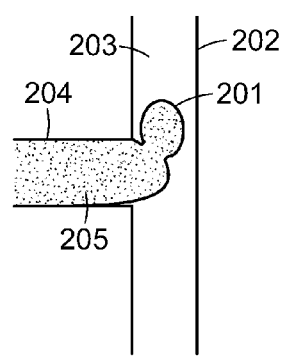
Figure 2C:
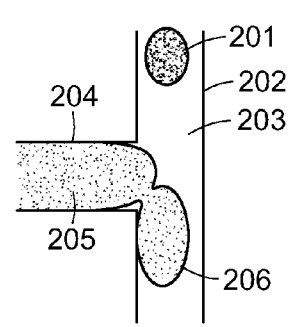
Figure 3A:
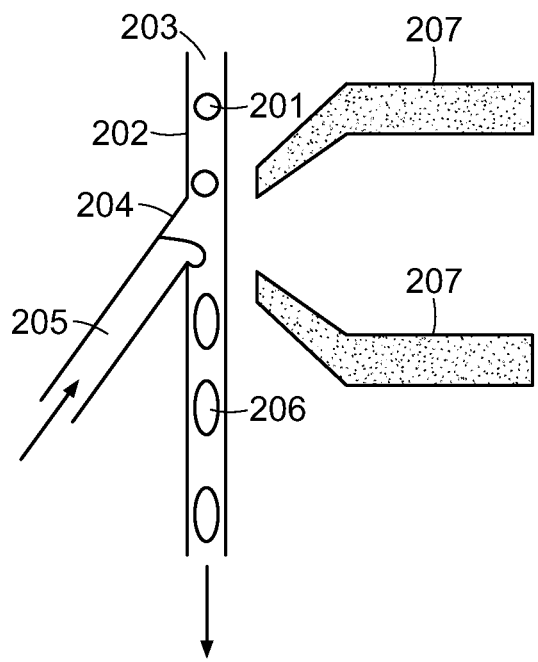
FIGS. 3A-3E show embodiments in which electrodes are used with methods of the invention to facilitate droplet merging. These figures show different positioning and different numbers of electrodes that may be used with methods of the invention.

FIGS. 2A-2C provide a schematic showing merging of sample fluids according to methods of the invention. Droplets 201 including either the first or second oligonucleotides flow through a first channel 202 separated from each other by immiscible carrier fluid and suspended in the immiscible carrier fluid 203. The droplets 201 are delivered to the merge area, i.e., junction of the first channel 202 with the second channel 204, by a pressure-driven flow generated by a positive displacement pump. While droplet 201 arrives at the merge area, a bolus of a second sample fluid 205 is protruding from an opening of the second channel 204 into the first channel 202 (FIG. 2A). FIGS. 2A-2C and FIG. 3B show the intersection of channels 202 and 204 as being perpendicular. However, any angle that results in an intersection of the channels 202 and 204 may be used, and methods of the invention are not limited to the orientation of the channels 202 and 204 shown in FIG. 2. For example, FIG. 3A shows an embodiment in which channels 202 and 204 are not perpendicular to each other. The droplets 201 shown in FIGS. 2A-2C are monodispersive, but non-monodispersive drops are useful in the context of the invention as well. The bolus of the second sample fluid stream 205 continues to increase in size due to pumping action of a positive displacement pump connected to channel 204, which outputs a steady stream of the second sample fluid 205 into the merge area. The flowing droplet 201 containing the first sample fluid eventually contacts the bolus of the second sample fluid 205 that is protruding into the first channel 202. Contact between the two sample fluids results in a portion of the second sample fluid 205 being segmented from the second sample fluid stream and joining with the first sample fluid droplet 201 to form a mixed droplet 206 (FIGS. 2B-2C). FIG. 12 shows an arrangement that was employed to form a mixed droplet in which a droplet of a first fluid was brought into contact with a bolus of a second sample fluid stream, in which the bolus was segmented from the second fluid stream and merged with the droplet to form a mixed droplet in an immiscible carrier fluid. FIG. 12A shows the droplet approaching the growing bolus of the second fluid stream. FIG. 12B shows the droplet merging and mixing with the bolus of the second fluid stream. In certain embodiments, each incoming droplet 201 of first sample fluid is merged with the same amount of second sample fluid 205.

In order to achieve the merge of the first and second sample fluids, the interface separating the fluids must be ruptured. In certain embodiments, this rupture can be achieved through the application of an electric charge. In certain embodiments, the rupture will result from application of an electric field. In certain embodiments, the rupture will be achieved through non-electrical means, e.g. by hydrophobic/hydrophilic patterning of the surface contacting the fluids.

Figure 3B:
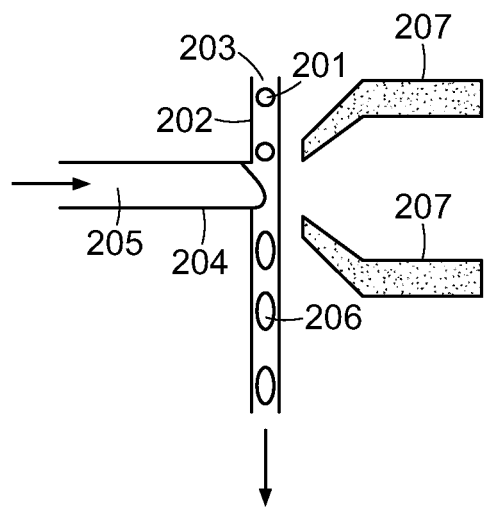
Figure 3C:
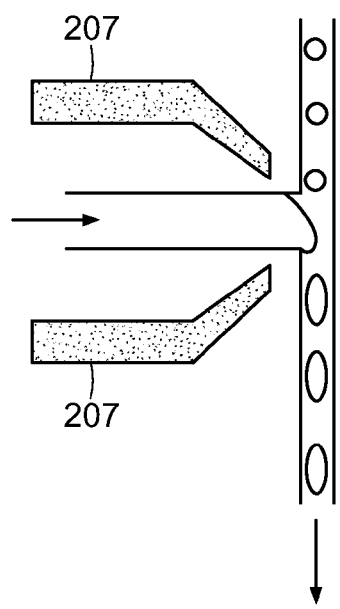
Figure 3D:
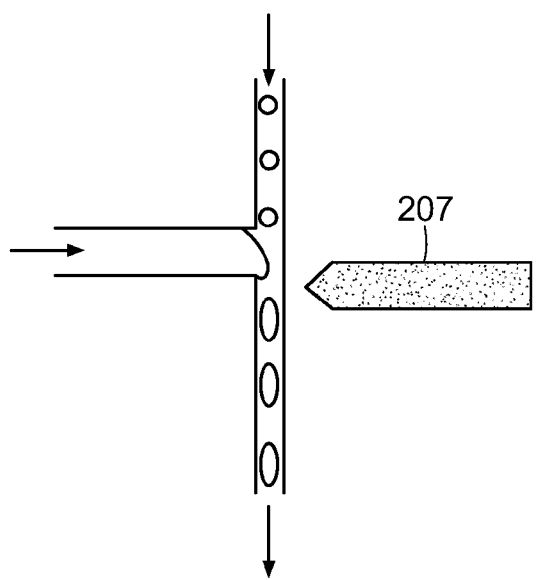
Figure 3E:
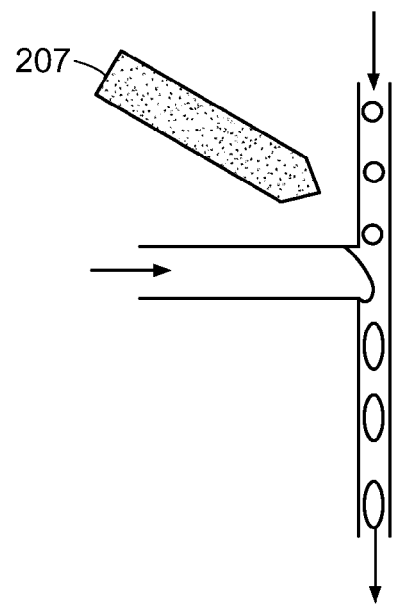
Figure 4:
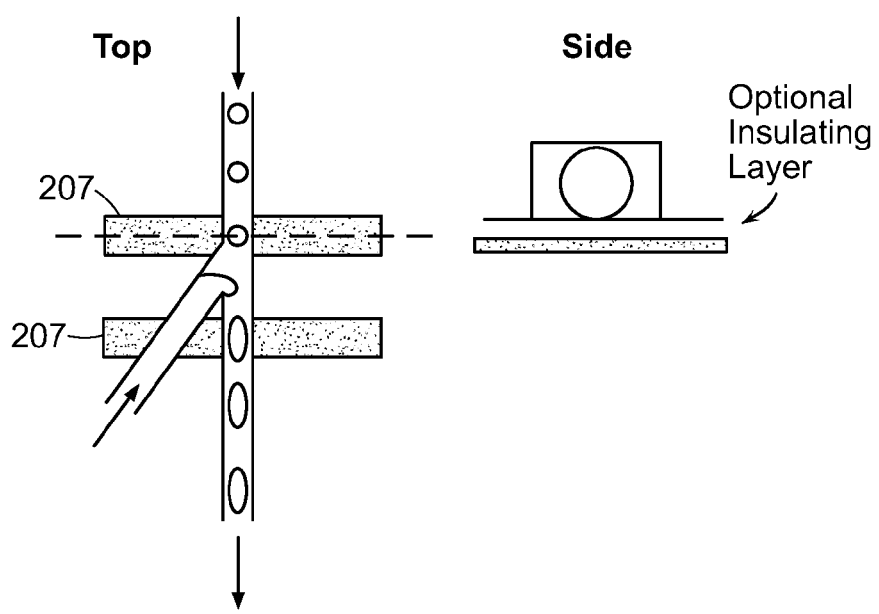
FIG. 4 shows an embodiment in which the electrodes are positioned beneath the channels.

In certain embodiments, an electric charge is applied to the first and second sample fluids (FIGS. 3A-3E). Any number of electrodes may be used with methods of the invention in order to apply an electric charge. FIGS. 3A-3C show embodiments that use two electrodes 207. FIGS. 3D-3E show embodiments that use one electrode 207. The electrodes 207 may positioned in any manner and any orientation as long as they are in proximity to the merge region. In FIGS. 3A-3B and 3D, the electrodes 207 are positioned across from the merge junction. In FIGS. 3C and 3E, the electrodes 207 are positioned on the same side as the merge junction. In certain embodiments, the electrodes are located below the channels (FIG. 4). In certain embodiments, the electrodes are optionally separated from the channels by an insulating layer (FIG. 4).

Description of applying electric charge to sample fluids is provided in Link et al. (U.S. patent application number 2007/0003442) and European Patent Number EP2004316, the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, saw tooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid 205 and the droplet 201. Rupturing the interface facilitates merging of the bolus of the second sample fluid 205 and the first sample fluid droplet 201 (FIG. 2B). The forming mixed droplet 206 continues to increase in size until it a portion of the second sample fluid 205 breaks free or segments from the second sample fluid stream prior to arrival and merging of the next droplet containing the first sample fluid (FIG. 2C). The segmenting of the portion of the second sample fluid from the second sample fluid stream occurs as soon as the force due to the shear and/or an elongation flow that is exerted on the forming mixed droplet 206 by the immiscible carrier fluid overcomes the surface tension whose action is to keep the segmenting portion of the second sample fluid connected with the second sample fluid stream. The now fully formed mixed droplet 206 continues to flow through the first channel 206.

Figure 5:
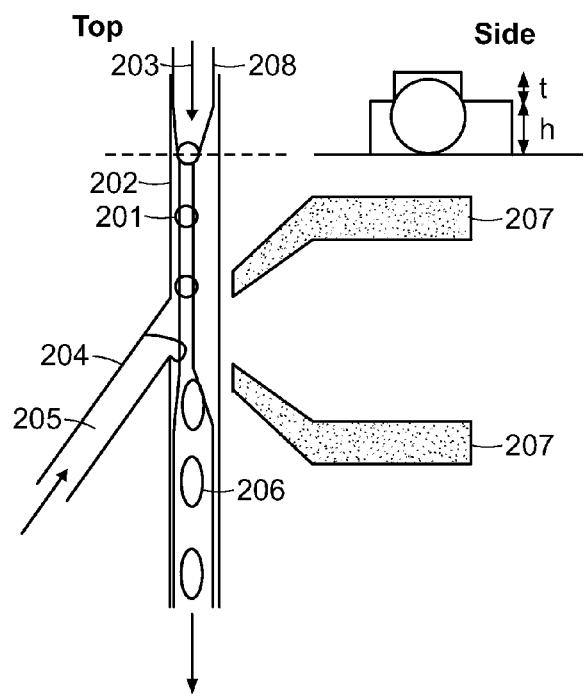
FIG. 5 shows an embodiment of forming a mixed droplet in the presence of electric charge and with use of a droplet track.

FIG. 5 illustrates an embodiment in which a drop track 208 is used in conjunction with electrodes 207 to facilitate merging of a portion of the second fluid 205 with the droplet 201. Under many circumstances it is advantageous for microfluidic channels to have a high aspect ratio defined as the channel width divided by the height. One advantage is that such channels tend to be more resistant against clogging because the "frisbee" shaped debris that would otherwise be required to occlude a wide and shallow channel is a rare occurrence. However, in certain instances, high aspect ratio channels are less preferred because under certain conditions the bolus of liquid 205 emerging from the continuous phase channel into merge may dribble down the side of the merge rather than snapping off into clean uniform merged droplets 206. An aspect of the invention that ensures that methods of the invention function optimally with high aspect ratio channels is the addition of droplets "tracks" 208 that both guide the droplets toward the emerging bolus 205 within the merger and simultaneously provides a microenvironment more suitable for the snapping mode of droplet generation. A droplet track 208 is a trench in the floor or ceiling of a conventional rectangular microfluidic channel that can be used either to improve the precision of steering droplets within a microfluidic channel and also to steer droplets in directions normally inaccessible by flow alone. The track could also be included in a side wall. FIG. 5 shows a cross-section of a channel with a droplet track 208. The channel height (marked "h") is the distance from the channel floor to the ceiling/bottom of the track 208, and the track height is the distance from the bottom of the track to the channel floor ceiling (marked "t"). Thus the total height within the track is the channel height plus the track height. In a preferred embodiment, the channel height is substantially smaller than the diameter of the droplets contained within the channel, forcing the droplets into a higher energy "squashed" conformation. Such droplets that encounter a droplet track 208 will expand into the track spontaneously, adopting a lower energy conformation with a lower surface area to volume ratio. Once inside a track, extra energy is required to displace the droplet from the track back into the shallower channel. Thus droplets will tend to remain inside tracks along the floor and ceiling of microfluidic channels even as they are dragged along with the carrier fluid in flow. If the direction along the droplet track 208 is not parallel to the direction of flow, then the droplet experiences both a drag force in the direction of flow as well as a component perpendicular to the flow due to surface energy of the droplet within the track. Thus the droplet within a track can displace at an angle relative to the direction of flow which would otherwise be difficult in a conventional rectangular channel.

Figure 6:
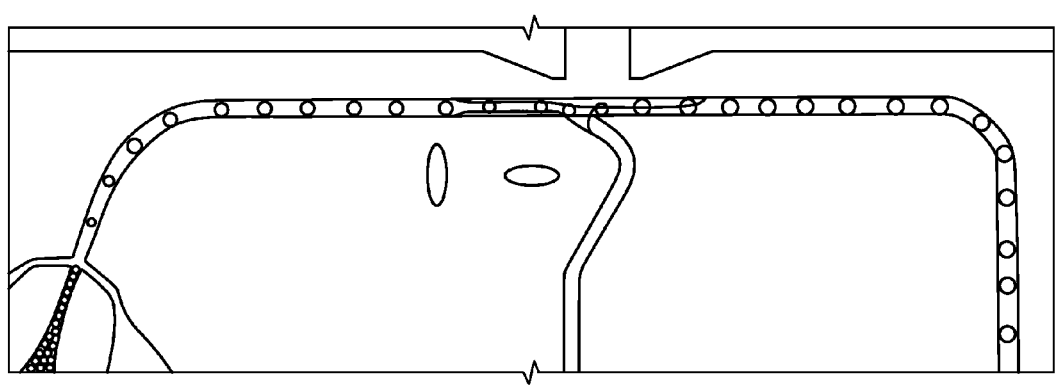
FIG. 6 shows a photograph capturing real-time formation of mixed droplets in the presence of electric charge and with use of a droplet track.

In FIG. 5, droplets 201 of the first sample fluid flow through a first channel 202 separated from each other by immiscible carrier fluid and suspended in the immiscible carrier fluid 203. The droplets 201 enter the droplet track 208 which steers or guides the droplets 201 close to the where the bolus of the second fluid 205 is emerging from the second channel 204. The steered droplets 201 in the droplet track 208 are delivered to the merge area, i.e., junction of the first channel 202 with the second channel 204, by a pressure-driven flow generated by a positive displacement pump. While droplet 201 arrives at the merge area, a bolus of a second sample fluid 205 is protruding from an opening of the second channel 204 into the first channel 202. The bolus of the second sample fluid stream 205 continues to increase in size due to pumping action of a positive displacement pump connected to channel 204, which outputs a steady stream of the second sample fluid 205 into the merge area. The flowing droplet 201 containing the first sample fluid eventually contacts the bolus of the second sample fluid 205 that is protruding into the first channel 202. The contacting happens in the presence of electrodes 207, which provide an electric charge to the merge area, which facilitates the rupturing of the interface separating the fluids. Contact between the two sample fluids in the presence of the electric change results in a portion of the second sample fluid 205 being segmented from the second sample fluid stream and joining with the first sample fluid droplet 201 to form a mixed droplet 206. The now fully formed mixed droplet 206 continues to flow through the droplet trap 208 and through the first channel 203. FIG. 6 shows a droplet track that was employed with methods of the invention to steer droplets away from the center streamlines and toward the emerging bolus of the second fluid on entering the merge area. This figure shows that a mixed droplet was formed in the presence of electric charge and with use of a droplet track.

Figure 7A:
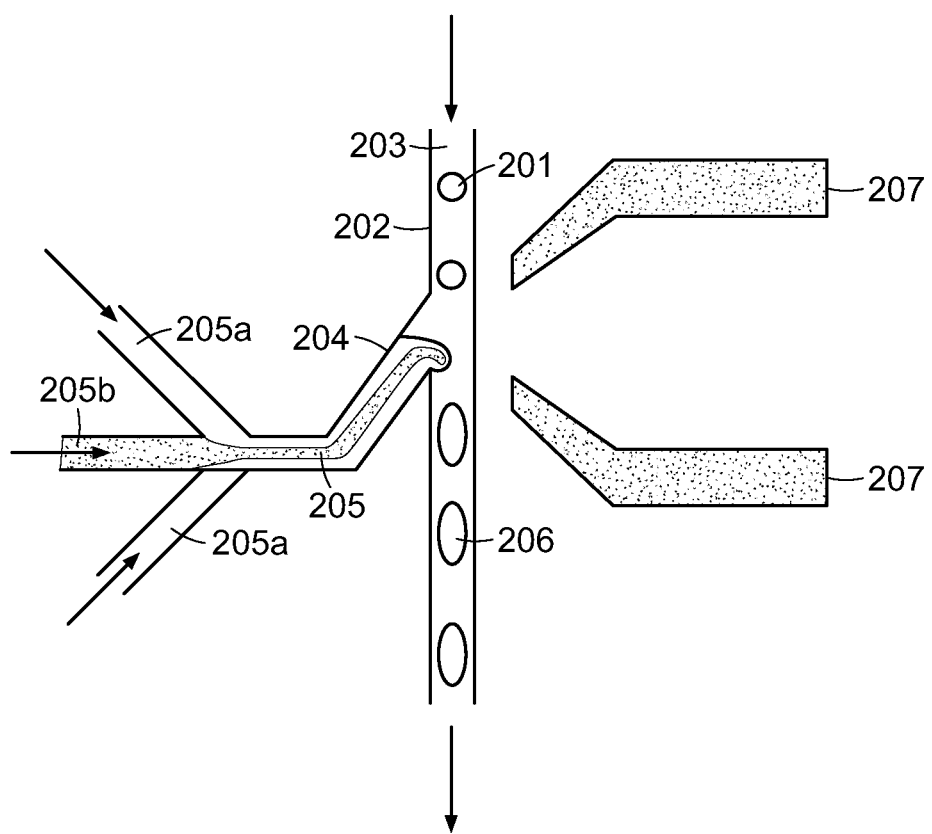
FIGS. 7A-7B show an embodiment in which the second sample fluid includes multiple co-flowing streams of different fluids.
Figure 7B:
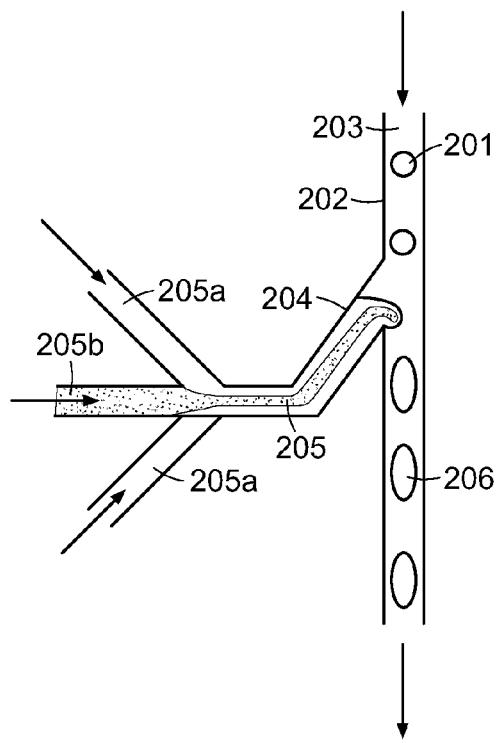

In certain embodiments, the second sample fluid 205 may consist of multiple co-flowing streams of different fluids. Such embodiments are shown in FIGS. 7A-7B. FIG. 7A is with electrodes and FIG. 7B is without electrodes. In these embodiments, sample fluid 205 is a mixture of two different sample fluids 205a and 205b. Samples fluids 205a and 205b mix upstream in channel 204 and are delivered to the merge area as a mixture. A bolus of the mixture then contacts droplet 201. Contact between the mixture in the presence or absence of the electric charge results in a portion of the mixed second sample fluid 205 being segmented from the mixed second sample fluid stream and joining with the first sample fluid droplet 201 to form a mixed droplet 206. The now fully formed mixed droplet 206 continues to flow through the through the first channel 203.

Figure 8:
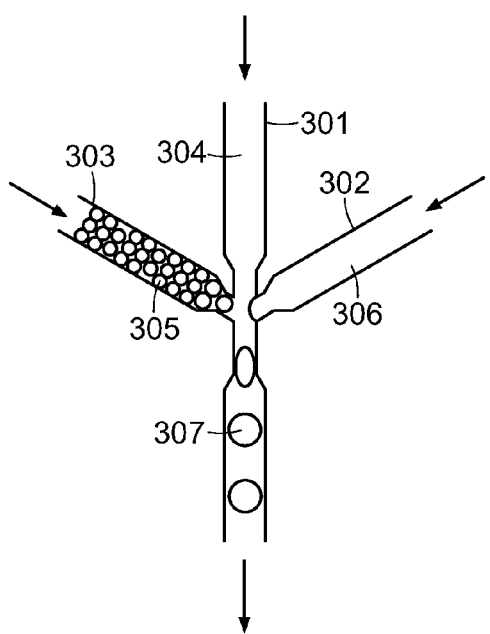
FIG. 8 shows a three channel embodiment for forming mixed droplets. This figure shows an embodiment without the presence of an electric field.
Figure 9:
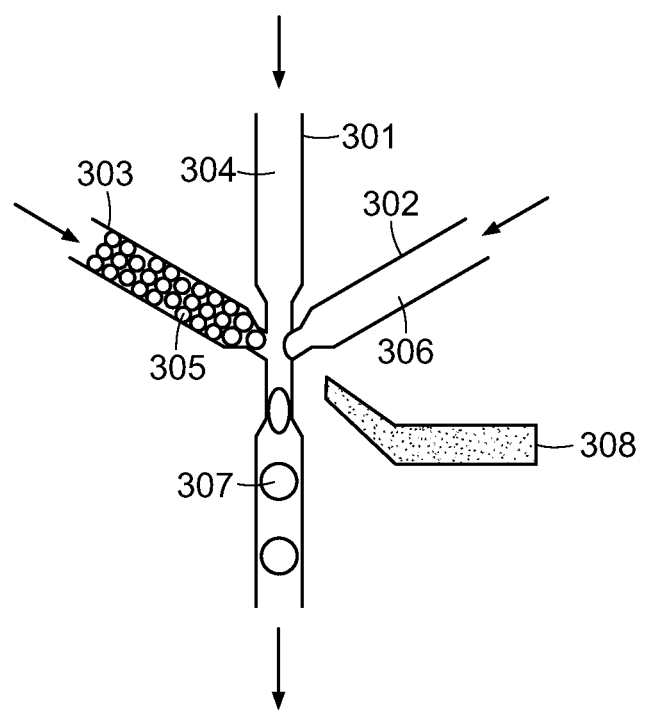
FIG. 9 shows a three channel embodiment for forming mixed droplets.

FIG. 8 shows a three channel embodiment. In this embodiment, channel 301 is flowing immiscible carrier fluid 304. Channels 302 and 303 intersect channel 301. FIG. 8 shows the intersection of channels 301-303 as not being perpendicular, and angle that results in an intersection of the channels 301-303 may be used. In other embodiments, the intersection of channels 301-303 is perpendicular. Channel 302 include a plurality of droplets 305 of a first sample fluid, while channel 303 includes a second sample fluid stream 306. In certain embodiments, a droplet 305 is brought into contact with a bolus of the second sample fluid 306 in channel 301 under conditions that allow the bolus of the second sample fluid 306 to merge with the droplet 305 to form a mixed droplet 307 in channel 301 that is surrounded by carrier fluid 304. In certain embodiments, the merging is in the presence of an electric charge provided by electrode 308 (FIG. 9). In certain embodiments, channel 301 narrows in the regions in proximity to the intersection of channels 301-303. However, such narrowing is not required and the described embodiments can be performed without a narrowing of channel 301.

Figure 10:
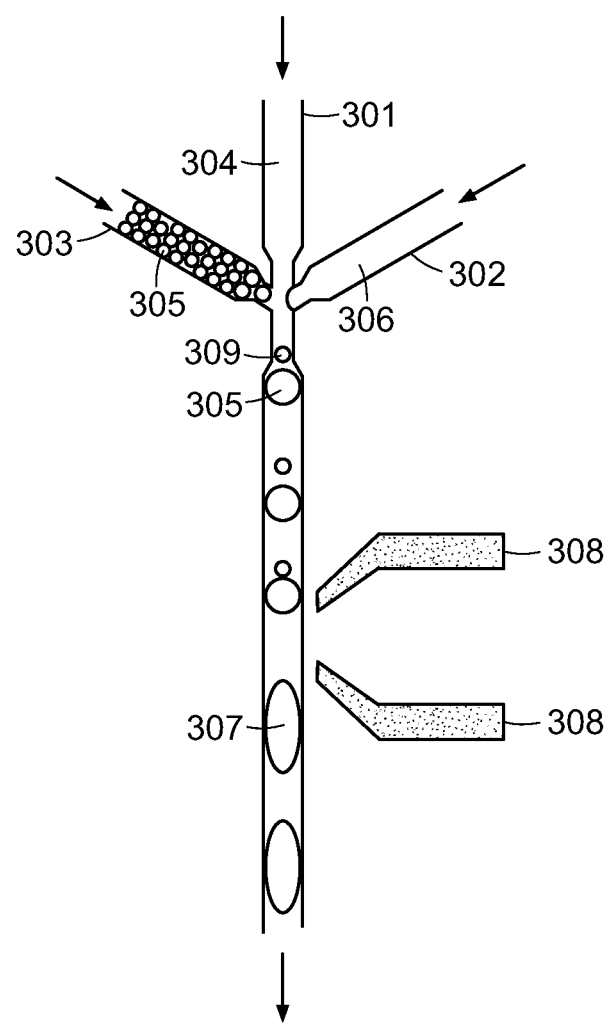
FIG. 10 shows a three channel embodiment for forming mixed droplets. This figure shows a droplet not merging with a bolus of the second sample fluid. Rather, the second sample fluid enters the channel as a droplet and merges with a droplet of the first sample fluid at a point past the intersection of the channels.

In certain embodiments, it is desirable to cause the droplet 305 and the bolus of the second sample fluid 306 to enter channel 301 without merging, as shown in FIG. 10. In these embodiments, the bolus of the second sample fluid 306 breaks-off from the second sample fluid stream and forms a droplet 309. Droplet 309 travels in the carrier fluid 304 with droplet 305 that has been introduced to channel 301 from channel 303 until conditions in the channel 301 are adjusted such that droplet 309 is caused to merge with droplet 305. Such a change in conditions can be turbulent flow, change in hydrophobicity, or as shown in FIG. 10, application of an electric charge from an electrode 308 to the fluids in channel 301. Application of the electric charge, causes droplets 309 and 305 to merge and form mixed droplet 307.

In embodiments of the invention, the size of the orifice at the merge point for the channel through which the second sample fluid flows may be the smaller, the same size as, or larger than the cross-sectional dimension of the channel through which the immiscible carrier fluid flows. FIGS. 11A-11C illustrate these embodiments. FIG. 11A shows an embodiment in which the orifice 401 at the merge point for the channel 402 through which the second sample fluid flows is smaller than the cross-sectional dimension of the channel 403 through which the immiscible carrier fluid flows. In these embodiments, the orifices 401 may have areas that are 90% or less than the average cross-sectional dimension of the channel 403. FIG. 11B shows an embodiment in which the orifice 401 at the merge point for the channel 402 through which the second sample fluid flows is the same size as than the cross-sectional dimension of the channel 403 through which the immiscible carrier fluid flows. FIG. 11C shows an embodiment in which the orifice 401 at the merge point for the channel 402 through which the second sample fluid flows is larger than the cross-sectional dimension of the channel 403 through which the immiscible carrier fluid flows.

Amplification Reaction in Partitions

FIG. 15 provides an illustrative example of an embodiment comprising components for a second amplification step, which may be an exponential amplification or second linear amplification. For example, for an exponential amplification FIG. 15 illustrates the products from linear amplification of the first pool as described above (e.g. forward strand amplification) combined with a primer species that recognizes the universal portion of the linear amplification products (e.g. U'$_A$) and a construct comprising a loci specific reverse primer and a second universal portion (e.g. U$_B$). FIG. 15 also illustrates an exemplary product from the amplification that comprises a locus region flanked on one side (e.g. 5' end) by a construct comprising, a universal portion a variable region (e.g. unique sequence tag), a pool identifier tag, and a locus specific primer region, and on the other side (e.g. 3' end) a construct comprising a universal portion, and a locus specific primer region.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as RE 41,780) and European publication number EP2047910 to RainDance Technologies Inc. The content of each of which is incorporated by reference herein in its entirety.

As described elsewhere in this description, the described embodiments include conducting reactions with biological entities within the emulsion droplets. An example of a very useful class of reactions includes nucleic acid amplification methods. The term "amplification" as used herein generally refers to the production of substantially identical copies of a nucleic acid sequence (typically referred to as "amplicons"). One of the most well-known amplification strategies is the polymerase chain reaction (also referred to as PCR) (e.g., Dieffenbach and Dveksler, PCR Primer, a Laboratory Manual, Cold Spring Harbor Press, Plainview, N.Y. [1995]). The amplification reaction may include any amplification reaction known in the art that amplifies nucleic acid molecules, such as Loop-mediated Isothermal Amplification (also referred to as LAMP), Recombinase Polymerase Amplification (also referred to as RPA), Helicase-dependent amplification (HDA), Nicking enzyme amplification reaction (NEAR), polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification (SDA), transcription based amplification system, nucleic acid sequence-based amplification, rolling circle amplification, and hyper-branched rolling circle amplification.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets. The merging of droplets can be accomplished using, for example, one or more droplet merging techniques described for example in Link et al. (U.S. patent application numbers 2008/0014589, 2008/0003142, and 010/0137163) and European publication number EP2047910 to RainDance Technologies Inc. In embodiments involving merging of droplets, two droplet formation modules are used. In one embodiment, a first droplet formation module produces the sample droplets consistent with limiting or terminal dilution of target nucleic acid. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acid, the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

In certain embodiments, the droplet formation modules are arranged and controlled to produce an interdigitation of sample droplets and PCR reagent droplets flowing through a channel. Such an arrangement is described for example in Link et al. (U.S. patent application Nos. 2008/0014589, 2008/0003142, and 2010/0137163) and European publication number EP2047910 to RainDance Technologies Inc.

A sample droplet is then caused to merge with a PCR reagent droplet, producing a droplet that includes the PCR master mix, primers, detectably labeled probes, and the forward or reverse amplification product. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to RainDance Technologies Inc. Further description of producing and controlling dielectrophoretic forces on droplets to cause the droplets to merge is described in Link et al. (U.S. patent application number 2007/0003442) and European Patent Number EP2004316.

In another embodiment, called simple droplet generation, a single droplet formation module, or a plurality of droplet formation modules are arranged to produce droplets from a mixture already containing the forward or reverse amplification product, the PCR master mix, primers, and detectably labeled probes. In yet another embodiment, called co-flow, upstream from a single droplet formation module two channels intersect allowing two flow streams to converge. One flow stream contains one set of reagents and forward or reverse amplification product, and the other contains the remaining reagents. In the preferred embodiment for co-flow, the template DNA and the PCR master mix are in one flow stream, and the primers and probes are in the other. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the forward or reverse amplification product in each droplet. In certain embodiments, the droplets are collected off chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001).

In certain embodiments, the three temperature zones are controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. Methods for controlling the temperature in each zone may include but are not limited to electrical resistance, peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their storage either on the same chip or another chip or off chip in some type of storage vessel such as a PCR tube. The chip or storage vessel containing the droplets is then cycled using standard instrumentation in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

Pooling, Release from Partitions, and Attaching Sequence Adapters

In certain embodiments, droplets are pooled via a "creaming" approach to separate the droplets from a substantial portion of the oil. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

In some embodiments, the creamed droplets are then placed onto a second carrier fluid which contains a destabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begin to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use of secondary PCR primers that recognize the universal portion of the amplified products. Once the amplicons are removed from the droplets, another set of secondary PCR primers that can hybridize to the universal regions of the amplicons can be used to amplify the products through additional rounds of PCR. The secondary primers can exactly match the universal region in length and sequence or can themselves contain additional sequence at the 5' ends of the tail portion of the primer.

During PCR cycling these additional regions also become incorporated into the amplicons. These additional sequences can include, but are not limited to: adaptor regions utilized by sequencing platforms for library preparation; barcode sequences for the identification of samples multiplexed into the same reaction; molecules for the separation of amplicons from the rest of the reaction materials (e.g., biotin, digoxin, peptides, or antibodies); or molecules such as fluorescent markers that can be used to identify the fragments.

Purification of the resulting amplicons is accomplished by methods well known in the art, for example using PCR product purification kits (Qiagen). The purified PCR product is portioned into two samples using, for example, automated means, for example microfluidic devices described herein, wherein the amplicons are compartmentalized into droplets and the population of droplets is portioned into a first population and a second population.

Sequencing

In the described embodiments, the amplified target molecules are sequenced using any suitable sequencing technique known in the art. In one example, the sequencing is single-molecule sequencing-by-synthesis. Single-molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety. Other examples of sequencing nucleic acids may include Maxam-Gilbert techniques, Sanger type techniques, Sequencing by Synthesis methods (SBS), Sequencing by Hybridization (SBH), Sequencing by Ligation (SBL), Sequencing by Incorporation (SBI) techniques, massively parallel signature sequencing (MPSS), polony sequencing techniques, nanopore, waveguide and other single molecule detection techniques, reversible terminator techniques, or other sequencing technique now known or that may be developed in the future.

A specific example of a sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing. Oligonucleotide adaptors are then ligated to the ends of the target nucleic acid molecules. The adaptors serve as primers for amplification and sequencing of the target nucleic acid molecules. Clonal copies of the target nucleic acid molecules are attached to DNA capture beads via amplification using adaptor sequence elements. For example, the copies of the target nucleic acid molecules attached to the beads are PCR amplified within droplets of an oil-water emulsion. The result is multiple copies of clonally amplified DNA fragments on each bead. In the next step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase and luciferase uses the ATP to generate light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. Oligonucleotide adaptors are ligated to the ends of target nucleic acid molecules. The adaptors serve as primers for amplification and sequencing of the target nucleic acid molecules. The target nucleic acid molecules can be attached to a surface. Addition of one or more nucleotides to a newly synthesized complementary strand via a polymerase releases a proton (H+) for incorporated nucleotide, which signal detected and recorded in a sequencing instrument. The signal strength is proportional to the number of nucleotides incorporated.

Ion Torrent sequencing employs a mode of detection which uses a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer releases the proton (H+) that causes a change in pH in the reaction chamber can be detected by a change in current by a chemFET. An array can have multiple chemFET sensors.

Another example of a sequencing technology that can be used in the methods of the provided invention is Illumina sequencing. Illumina sequencing is based on the amplification of DNA on a solid surface using fold-back PCR and anchored primers. Adapters are added to the 5' and 3' ends of the target nucleic acid molecules. Target nucleic acid molecules are attached to the surface of flow cell channels are extended and bridge amplified. The target nucleic acid molecules become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Sequence Analysis

In some embodiments a sequence reconstruction process may be needed to assemble short reads into longer sequence elements. Typical sequence reconstruction includes bioinformatically finding overlaps of the ends of sequence reads and combining to form a "contiguous sequence" (also referred to as a contig). To be able to do that unambiguously, one must ensure that sequenced fragments are distinct enough, and do not have similar stretches of DNA that will make assembly from short fragments ambiguous (e.g. repeating sequence elements).

In addition to de-novo assembly fragments can be used to obtain phasing (assignment to homologous copies of chromosomes) of genomic variants, by observing that under conditions of experiment described in the preferred embodiment long fragments originate from either one of chromosomes, which enables to correlate and co-localize variants detected in overlapping fragments obtained from distinct partitioned portions.

Methods for analyzing sequence reads are known in the art. Thus the embodiments of the invention makes it possible to identify various types of rare events example of which may occur in cancer such as breast cancer, stomach and esophagus cancer, colorectal cancer, lung cancer, central nervous system cancer, thyroid cancer, pancreatic cancer, prostate cancer, head and neck cancer, skin cancer, bladder cancer, liver cancer, kidney cancer, gastric cancer, melanoma, sarcoma, gynecological (cervix, ovary, uterus) cancer, endometrial cancer, and/or different types of leukemia and lymphoma. Thus, embodiments of the invention may be used for the diagnosis, prognosis, treatment and/or monitoring of other types of cancer can be devised by those skilled in the art by identifying specific variation in a sample, depending on the specific type of cancer being screened for (e.g. brain cancer, breast cancer, ovarian cancer, prostate cancer, lung cancer, skin cancer, and the like) and the purpose of the screening (e.g. diagnostic, prognostic, treatment selection, patient monitoring). Embodiments of the invention also make it possible to definitively identify de novo variation as true variation rather than sequencing errors. Such de novo variation may be cross-referenced with additional population information (disease, race, etc.) to produce new biomarkers.

In the presently described embodiments, the unique sequence tag portion of each sequence read is analyzed and reads corresponding to the same sequence composition of the unique sequence tag grouped and compared to identify variation within the group (e.g. a false positive event) and/or agreement of variation in the group from a consensus sequence (e.g. true variation). Additionally, the sequence reads are analyzed to confirm that the same variation is found in groups from both the forward and reverse strands. A variation that is found to originate from multiple different nucleic acid molecules from the sample is considered a true variation whose frequency in the sample can be accurately calculated based on the count of different nucleic acid molecules from the sample were found to carry the variation.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:
1. A method comprising the steps of:
providing a nucleic acid sample divided into a first pool and a second pool;
producing a first strand product from a forward strand of nucleic acid from the first pool and a first strand product from a reverse strand of nucleic acid from the second pool, wherein the first strand product from the forward strand and the reverse strand each comprise a unique sequence tag that comprises a sequence composition different from each other;
compartmentalizing the first strand products from the forward strand and the reverse into compartmentalized portions, wherein a plurality of the compartmentalized portions comprise only a single first strand product; and
amplifying the forward and reverse strand amplification products in the compartmentalized portions.

2. The method according to claim 1, further comprising:
producing a plurality of first strand products from the forward strand and a plurality of first strand products from the reverse strand, wherein the first strand products from the forward strand and the reverse strand each comprise a unique sequence tag that comprises a sequence composition different from all other unique sequence tags among the strand products.

3. The method according to claim 2, wherein:
the plurality of first strand products from the forward strand and the plurality of first strand products from the reverse strand, comprise products from a plurality of different loci.

4. The method according to claim 1, wherein:
the amplification is an exponential amplification.

5. The method according to claim 4, wherein:
the exponential amplification comprises PCR.

6. The method according to claim 1, wherein:
the first strand products are produced by a polymerase extension reaction.

7. The method according to claim 6, wherein:
the polymerase extension reaction employs primers comprising a nucleic acid molecule target specific region, a pool identification tag, a unique sequence tag, and a first universal portion.

8. The method according to claim 1, wherein:
the first strand products are produced by a ligation reaction.

9. The method according to claim 1, further comprising:
sequencing products of the amplifying step to produce a plurality of sequence reads;
analyzing the sequence reads to identify a variant from a consensus sequence in a plurality of the sequence reads that comprise a unique sequence tag sequence composition that is the same; and
correlating an identified variant from the forward strand with an identified variant from the reverse strand that is complementary to the forward strand.

10. The method according to claim 9, wherein the variant is associated with a disease.

11. The method according to claim 10, wherein the disease is cancer.

12. The method according to claim 9, wherein prior to the sequencing step, the method further comprises incorporating sequencing adaptors with the products of the amplifying step.

13. The method according to claim 9, wherein sequencing is sequencing-by-synthesis.

14. The method according to claim 1, wherein the first strand products from the forward strand and the reverse strand are pooled together prior to the compartmentalizing step.

15. The method according to claim 1, wherein the first strand products from the forward strand and the reverse strand are maintained separately prior to the compartmentalizing step.

16. The method according to claim 1, wherein first strand products from the forward strand and the reverse strand are in an aqueous fluid and compartmentalizing comprises partitioning the aqueous fluid with an immiscible fluid to form droplets of the aqueous fluid.

17. The method according to claim 16, wherein the aqueous fluid is flowing in a channel and the produced droplets are flowing in a channel.

18. The method according to claim 16, wherein the immiscible fluid is an oil.

19. The method according to claim 18, wherein the oil comprises a surfactant.

20. The method according to claim 19, wherein the surfactant is a fluorosurfactant.

21. The method according to claim 1, wherein the nucleic acid molecule is from a formalin-fixed paraffin-embedded sample.

22. The method according to claim 1, wherein the nucleic acid molecule is from a blood sample.

23. The method according to claim 1, wherein the nucleic acid molecule is from a cell free circulating nucleic acid sample.

* * * * *